United States Patent [19]
Mielordt

[11] Patent Number: 5,819,756
[45] Date of Patent: Oct. 13, 1998

[54] SMOKING OR INHALATION DEVICE

[76] Inventor: Sven Mielordt, Grossbeerenstrasse 81, D-10963 Berlin, Germany

[21] Appl. No.: 596,325
[22] PCT Filed: Aug. 17, 1994
[86] PCT No.: PCT/DE94/00991
  § 371 Date: Feb. 16, 1996
  § 102(e) Date: Feb. 16, 1996
[87] PCT Pub. No.: WO95/05094
  PCT Pub. Date: Feb. 23, 1995

[30] Foreign Application Priority Data

Aug. 19, 1993 [DE] Germany .......................... 43 28 243.1

[51] Int. Cl.⁶ ....................................................... A24F 1/10
[52] U.S. Cl. ........................... 131/330; 131/194; 131/196; 131/198.1
[58] Field of Search ..................................... 131/194, 196, 131/198.1, 330

[56] References Cited

U.S. PATENT DOCUMENTS

| | | | |
|---|---|---|---|
| 2,104,266 | 1/1938 | McCormick .......................... | 131/198.1 |
| 2,269,541 | 1/1942 | MacDonald ............................ | 131/196 |
| 4,328,795 | 5/1982 | Cabaniss, III ......................... | 131/180 |
| 4,524,782 | 6/1985 | Chister .................................. | 131/180 |
| 4,735,217 | 4/1988 | Gerth et al. ............................. | 131/273 |
| 4,771,796 | 9/1988 | Myer ..................................... | 131/273 |
| 4,907,606 | 3/1990 | Lilja et al. .............................. | 131/194 |
| 4,947,875 | 8/1990 | Brooks et al. .......................... | 131/194 |
| 5,179,966 | 1/1993 | Losee et al. ............................ | 131/351 |
| 5,285,798 | 2/1994 | Banerjee et al. ........................ | 131/194 |
| 5,322,075 | 6/1994 | Deevi et al. ............................ | 131/194 |

FOREIGN PATENT DOCUMENTS

| | | |
|---|---|---|
| 379942 | 10/1986 | Austria . |
| 0295122 | 12/1988 | European Pat. Off. . |
| 123446 | 5/1900 | Germany . |
| 3735704 | 5/1989 | Germany . |
| 4328243 | 3/1995 | Germany . |

Primary Examiner—Aaron J. Lewis
Attorney, Agent, or Firm—Spencer & Frank

[57] ABSTRACT

A device for smoking tobacco or another smoking product or for inhaling aerosols released by corresponding substances when they are heated. The substances that constitutes the smoking product is shredded, granulated or otherwise crushed. The smoking product contained in a reservoir that forms a substantially closed chamber is heated by convection by previously heated air up to a temperature below its glow temperature. An electric heating device that forms a heating air generator arranged in a channel is provided with an outlet nozzle for introducing the heated air into the chamber after the air runs through the heating device and absorbs heat energy. The smoking product is spread in a substantially even manner on a saucer-like surface in the chamber. The outlet nozzle is arranged in such a way that the heated air that flows out of the nozzle flows directly onto the smoking product and heats it through up to a temperature close to but lower than its glow temperature.

12 Claims, 7 Drawing Sheets

FIG. I

SMOKING OR INHALATION DEVICE

FIELD OF THE INVENTION

The invention discloses a device for inhaling an inhalable substance.

BACKGROUND OF THE INVENTION

The consumption of tobacco products by choice is a common form of recreational/social drug use. The smoking of tobacco does, however, entail the ingestion (through the respiratory system) of typical toxic by-products. Smokeable products develop these by-products at combustion temperatures of 800–1000 degrees centigrade; they consist of tar, condensate or heavily volatile carcinogenes as well as carbon monoxide and other toxic inorganic substances-heavy metals, for example; all in constrast to the usually mostly minimal toxic content of the drug itself. Experiments have shown that the release of alkaloids and active products (for example nicotine) which contribute to the enjoyment of smoking occur at temperatures as low as 100 degrees centigrade.

Such devices can also be used in the interests of health (the treatment of addiction to cigarettes, for example) by introducing pharmaceutically effective aerosols (released from substances reached by the air stream) to the air flow during the heating process. Hereinafter, "smoking product" refers to any smokeable product, including pharmaceutically effective aerosols.

A device already exists, namely the application number EP-A2 358002 or the DE-U-92 18 005.1, which heats the smoking product by means of a gas flow, preferably air, which has been electrically preheated. A battery-powered resistance heater has been provided for this purpose. The smoking product is convection heated to a temperature lower than that at which combustion occurs and harmful substances are able to form, or to a temperature at which the formation of these substances Is reduced, thus facilitating smoking enjoyment by releasing the relevant stimulating aerosols.

In the aformentioned device the smoking product is compressed to a cylindrical mass and heated air flows lenghtwise through the mass, always in the same direction. It should also be noted that it is not possible to move this mass—which varies from lightly to heavily compressed—in relation to the heated gas/fluid or the electrical heating source.

The disadvantage is that the heated air affects only the directly exposed surface areas of the smoking product and is thus able to heat only this surface area to the desired temperature, i.e. that at which aerosols are released which contribute to the enjoyment of smoking. After longer periods of exposure to the heated air, the smoking product can become subject to localised overheating. This overheating can in turn lead to carbonisation and combustion and the attendant possibility of the formation of toxic substances. Furthermore, the product will remain only partially consumed, since the greater part of It will not have been heated to a sufficient temperature. This not only leads to higher energy consumption (since the periods during which the product is heated are independent from the smoke's flow rate) but also to an inefficient and incomplete consumption of the product itself. Given the drawbacks of the current technology It is now the task to create a device of the aforementioned kind which enables, quite simply, a more or the most efficient consumption of a given smoking product and, more particularly, the creation of a desired smoking profile.

SUMMARY OF THE INVENTION

The invention is contingent upon the recognition that the effective and thorough exploitation of the substance from which aerosols are to be extracted is possible when the smoking product is evenly and, particularly, sequentially heated to a temperature below that at which it will combust and thus release harmful by-products. This condition in particular can be achieved if a relatively finely-distributed quantity of the smoking product—possibly in smaller discrete quantities—is convection heated by carrier gas flow, particularly air, directly onto the product in such a way as to ensure that the volume bodies of smoking product particles can be heated near the surface by the introduced carrier gas, directly affected, and warmed through as most as possible. Inasmuch as the smoking product is made of particles, such as, for example, tobacco strands, it may be referred to as a "particulate". This prevents what occurs in cartridge-like assemblies—carrier gas, which has already cooled down, reaches the interior parts of the compressed smoking product and is incapable of heating it at these points to the desired temperature. This is quite clearly inefficient and rules out the use of such devices as a basis for further design.

In the aforementioned cartridge-like assemblies, it would also be possible to heat the air to such a temperature that the inner areas of the smoking product would be sufficiently heated. This would, however, as mentioned previously, result in overheating and combustion of the surfaces first reached by the heated air. The resulting by-products are, as we have established, harmful and thus undesirable.

The desired temperatures can be achieved if the heat affected surface of a smoking product which has been chosen is large in ratio to the volume of the smoking product surrounded by this surface. A desired smoking profile may be software-determined by means, for example, of user-defined smoking product temperatures, corresponding feed rate of the smoking product as well as an oscillation of the relative position between product and hot air jet.

By means of the above mentioned temperature regulation, the formation of organic carcinogenes and the release of inorganic toxins (heavy metals and carbon monoxide) can be stopped or at the very least considerably reduced.

An advantageous further development of this invention would be to "pulse" heating; in this way the temperature of the product itself does not rise to that of combustion, when it is taken care of the thermal time constants acting in combination, even if the air is shortly super-heated. In this way it is possible at any time to rapidly reach the temperature at which the most efficient exploitation of the smoking product occurs, thus minimizing the amount of air at the initial phase of the heating process (enriched with only low concentration of aerosol) and corresponding loss of enjoyment for the consumer.

The temperature at which the smoking product "glows" provides a good criterion by which we can recognize the process, since the rapidly increasing red and infra-red radiation suggests the regulation or exclusion of hot air flow. This "glow" appears also with the use of inert gas as a heat carrier. By keeping track of the glow, one is able to control the process, even when using air as a carrier gas, since the air flow can be regulated before combustion occurs.

In a preferred embodiment of the invention, the entire quantity of the smoking product is distributed in a reservoir with several chambers of roughly equal size. Each chamber is convection heated by means of a jet of air which has been pre-heated to the required temperature In a hot air generator. The hot air generator is, in turn, powered by a (preferably)

electrical heating appliance. The air to be warmed is sucked or inhaled by the smoker from the air surrounding the device into the hot air generator. In order to heat up the entire quantity of smoking product sequentially and evenly and to be able to extract the maximum quantity of aerosol, discrete quantities are partially heated in lots. For this purpose it is possible to move the hot air jet or stream in relation to the smoking product. The reservoirs containing the smoking product are able to be moved while the hot air stream is fixed; this facilitates simpler operation. A shallow, cylindrical reservoir is slowly revolved by the inbuilt drive unit and thereby exposed in circular sections to the hot air stream. The circular reservoir is divided correspondingly into chambers of equal size, each containing an equal quantity of smoking product. For the generation of individual smoking profiles it is advantageous to be able to control the movement of the smoking product in relation to the quantity and temperature of the supplied air.

In order to stabilise the relative position of each discrete quantity of smoking product, it is advisable to use a restraint grille.

It is also possible to use pre-fabricated or pre-formed tablets or other flat-shaped bodies which can then be inserted into the device; they hold quantities of smoking product and can be directly affected by gas flow.

According to an advantageous further development of the invention, the reservoir forms a shallow cuboid and is provided with cubic compartments. A drive unit would be given to move the reservoir translatorily, thus warming the smoking product equally in each of the chambers. The movement under the hot air jet occurs steadily or gradually (stepped), controlled by a predetermined program.

The invention displays—at least in some respects—further advantages and possible directions for subsequent development:

In order to achieve constant heating independent of strength or quantity of inhalation of the smoker, flow-rate dependant regulation of electrical energy fed into the hot air generator would be employed. Making use of the physical correlation between flow velocity, quantity of fluid flow and flow pressure, the quantity of air transported from the air surrounding the machine into the hot air generator by the sucking or inhalation of the smoker would be measured by a differential pressure sensor and the value fed into a controller which would, in turn, supply the appropriate amount of heating power. In the case of low heat capacity of the heating appliance element, the desired temperature profile can be delivered within short periods of time.

The hot air generator allows the air to be heated in an electrical heating appliance, whereby air sucked from the environment will be raised to a temperature above that at which the pyrolytic formation of aerosol occurs in the smoking product. This super-heating is necessary in order to compensate for the inevitable heat loss /time constant between the heating inside the hot air generator and heating of the smoking product. A further possible development improvement: the heating appliance could be manufactured as a strip-shaped foil element. To lower flow resistance and increase surface contact of the foil element with the fluid flow to be heated, the foil would be bent into a U-shape and provided with several circular and/or slot-shaped openings on its surface. The U-shape is parallel to the flow direction of the air to be heated which flows into the U-shaped inlet. An additional improvement could be that the heating appliance be shaped tape-like, lightly bulbous, with side walls on whose surface would be enhancing protuberances such as circular nipples or conical fingers.

Another advantageous subsequent development of the invention is the employment of an inert gas in the convection heating of the smoking product; that would further reduce the development of harmful substances.

Optimized exploitation of the smoking product requires an almost isothermal heating of the discrete product quantities. Up to a point, physical laws will always result in the areas near the surface of the smoking product being primarily affected when coming into contact with the carrier gas flow.

Compared to the current technology, this invention displays very even heating of sequentially activated particles with a high degree of penetration relative to particle size, simply by directing the hot air flow onto the smoking product's relative thinness and large surface area. In this text, this fact will also be clarified by the terms "sequentially homogeneous", "equal" or "uniform".

When focusing radiation energy onto the volume area of the affected smoking product's zone, the release of aerosols can also be induced. The use of UV/visible light or short-wavelength infra-red radiation heats particles' surfaces to a temperature slightly higher than their interiors (as is the case with the use of hot air flow) since radiation is absorbed at the surface.

However, the use of longer wavelength radiation (microwave or radio frequencies, for example) will result in the absorption of radiation energy by the entire volume of the affected smoking product by virtue of (amongst other things) dielectrical losses in the high frequency field. In this way, particle cores become hotter than their surfaces, since the flow of carrier gas still needed for transportation of the smoking products' aerosol tends to cool the surfaces by convection.

An almost gradient-free heating of the particles at a given finite depth of penetration can thus be achieved: heated carrier gas is directed onto the particles which are simultaneously exposed to penetrating absorbable radiation energy. This would create such a temperature as to heat the particle cores to an even higher temperature than that of the hot-air affected particle surfaces, causing an increase of the aerosols' vapour pressure inside the particle cores and thus facilitating an increase in aerosol diffusion to the surface and an improvement of efficiency relative to toxicity.

Shock-pulse super-heating of particle cores by radiation can also be effective: the particle's structure becomes loosened, with the attendant increase of affected surface area. Focusing of radiation is usually annular or from at least two canted surfaces. The saucer for the smoking product can be made reflective.

It is advisable, when using software-controlled smoking profiles, to exploit the smoking product in several successive "recycling" phases. A feed rate can be established by moving the heat-affected zones of the smoking product in relation to sucked carrier gas volume and nominal temperature whereby the initial "draw" (the smoker's inhalation) requires little or no feed rate, since the smoking product needs to be heated up. When the entire surface area of the smoking product has been affected, the second phase begins—the temperature is increased and a higher feed rate introduced, the latter due to the approaching exhaustion of product. A third and final phase, where all parameters are progressively increased, will find the smoking product fully consumed and no longer smokeable. Particularly at high temperatures, it is favourable to have an overlapping oscillation of the relative position between hot carrier gas jet and the affected zone.

Subsequent advantegeous developments and improvements of the invention will be ennumerated in the subclaims or will be further detailed in the following text and in the diagrams of the preferred embodiments of the invention.

DETAILED DESCRIPTION OF THE INVENTION

Figure 1:
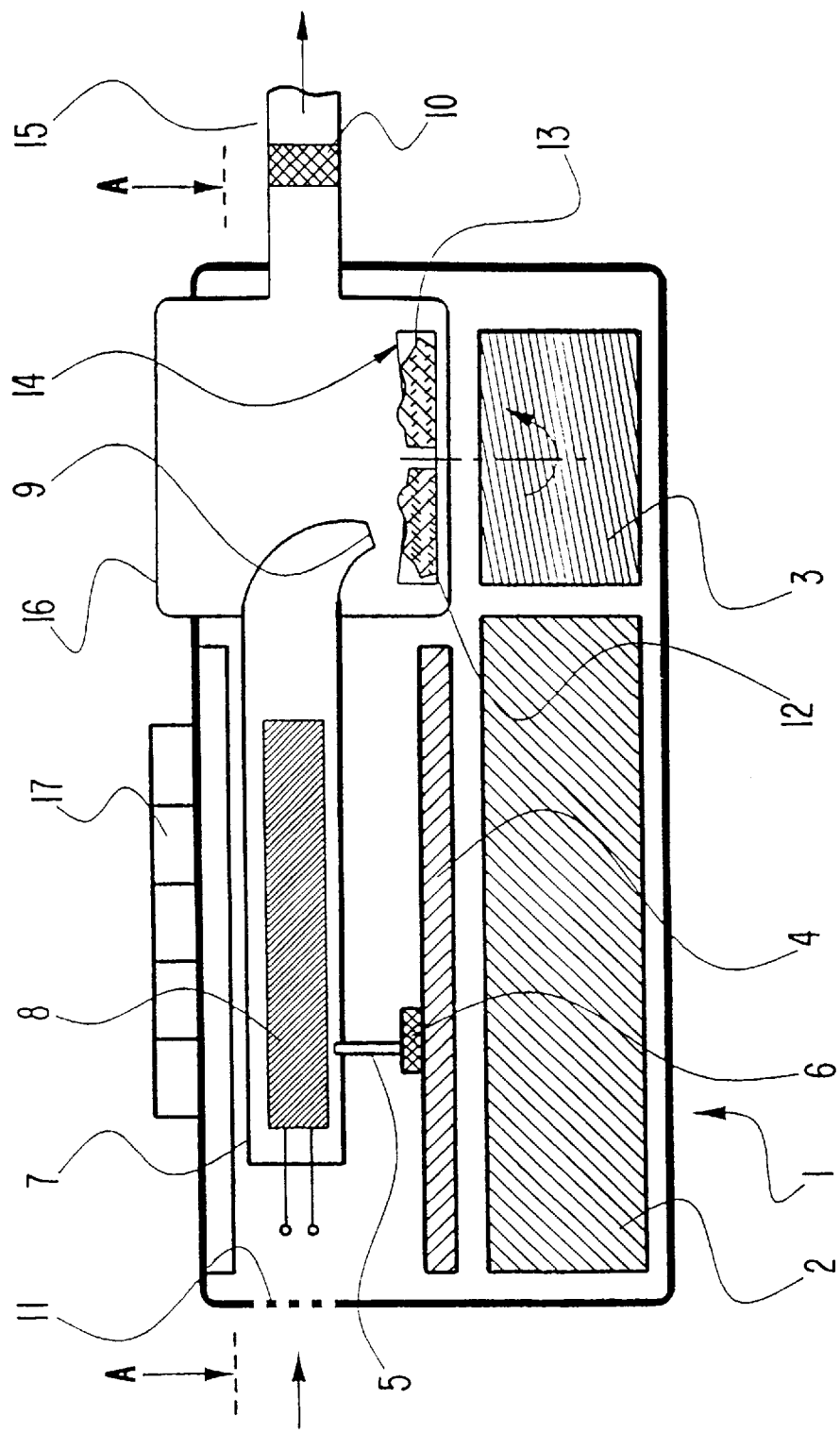
FIG. 1 is a schematic representation of a longitudinal cross-section through a preferred embodiment of the invention (across the A—A line in FIG. 2)

The appliance 1 depicted in FIG. 1 as a longitudinal cross-section across the line A . . . A of FIG. 2 for the smoking of tobacco or other smoking products is essentially equipped with a hot air generator 7. Heated air leaving the hot air generator 7 is used to convection heat the smoking product 13. The smoker inhales from a standpipe 15 the required quantity of air through an inlet 11 provided in the wall of the housing. In this flow path, the hot air generator 7 is integrated in such a way that ambient air sucked through the inlet 11 will reach the hot air generator 7 directly, to then flow along a heating appliance 8. This results in heating of the smoking product in areas near the surface.

The air outlet nozzle 9 of the hot air generator 7 is directed into the smoking chamber 16 of the smoking device 1, the outlet being positioned closely to the smoking product 13 in the reservoir 12. At this point, the heated air reaches a temperature at which the smoking product 13 becomes pyrolytically converted to release aerosols. Due to the convection heating of the smoking product 13, combustion which usually occurs at a minimum temperature of 800 degrees Centigrade (and the attendant formation of harmful products) can be prevented. It is advisable, for the formation of aerosols which contribute to the enjoyment of smoking, to heat the affected particle volumes sequentially, in an essentially even and uniform manner, to their respective pyrolysis temperatures. Because of this, the quantity of smoking product 13 in the reservoir 12 of the smoking chamber 16 is divided into several discrete quantities and distributed amongst the individual chambers 14 of the reservoir 12.

The drive unit 3 rotates the reservoir 12 so that the discrete quantities of smoking product are sequentially exposed to the hot air jet emerging from the outlet nozzle 9. Regardless of whether rotation of the reservoir (pre-programmed by a user-adjustable control unit) occurs steadily or in gradual steps, the quantities of smoking product will be uniformly heated and aerosols extracted with a high degree of efficiency. This provides a uniformly high degree of smoking enjoyment coupled with a highly efficient exploitation of the smoking product and, conversely, negligible losses. In order to fully exploit the smoking product, a uniform temperature of the hot air stream independent of inhalation strength is essential. A regulator is provided for this purpose; the pressure sensor 6 measures the flow velocity within the hot air generator 7 for the regulation of the (preferably electrically powered) heating appliance 8. The pressure sensor 6 is connected to the flow path by means of a tube 5.

To operate the smoking device 1, a battery 2 is provided for the drive unit 3 and the electronic module 4. The control panel 17, equipped with buttons, enables easy on/off switching of the device 1 and the adjustment of the required hot air's temperature range or of the drive unit's speed. In this manner it is possible, e.g. via software, to very simply choose a particular smoking profile. The envisaged filter 10 inside the standpipe 15 restrains undesired particles circulating within the smoking chamber 16.

Figure 2:
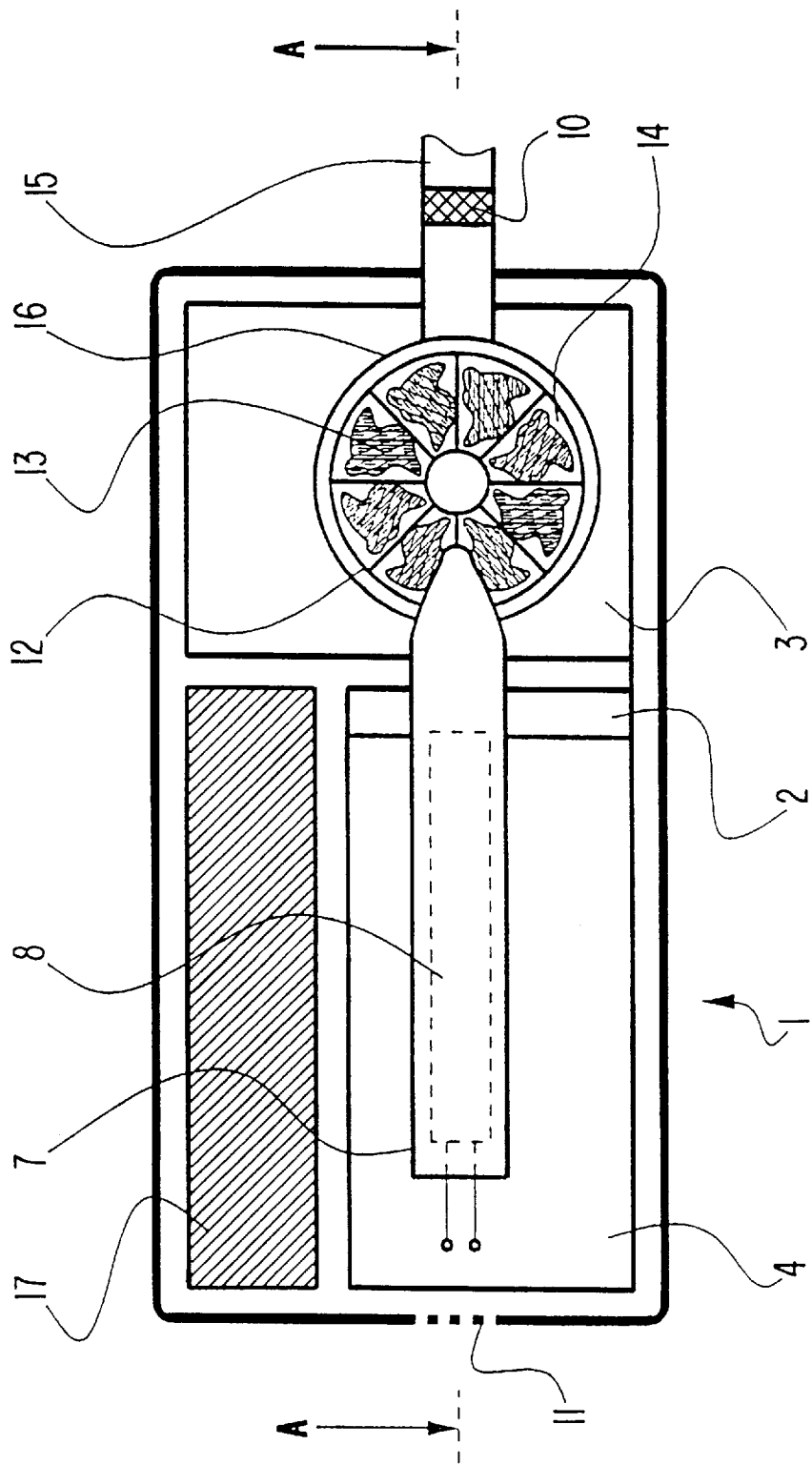
FIG. 2 shows another cross-section of this realization.

FIG. 2 is a cross-section along the line A . . . A of FIG. 1. The saucer-like, shallow cylindrical reservoir 12 is divided into several equal segments 14, each being filled with roughly equal quantities of the smoking product 13.

FIGS. 3, 3a–f depict further favourable developments of the invention, showing optimized realisations of the heating appliance 8 from FIGS. 1–2 in schematic form. The heating appliance 8 is a foil element (FIG. 3); the foil 24 is U-shaped and air flows between the inner sides of the U. Air flow 23 is admitted through the apertures 25a–d, an implementation or a combination of circular and/or geometrical slots. The heating foil 24 is capable of an advantageously low heat capacity, thus optimising the conditions required for the generation of particular smoking profiles, for the maximum possible consumption of the smoking product, and to facilitate the extraction of the remaining aerosol from chamber 16 without releasing new aerosol from the smoking product 13.

Figure 3:
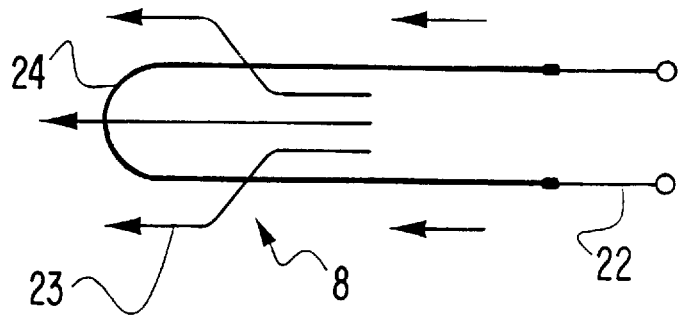
FIG. 3 to 3f demonstrate further advantageous developments of the invention shown in FIGS. 1–2.
Figure 3A:
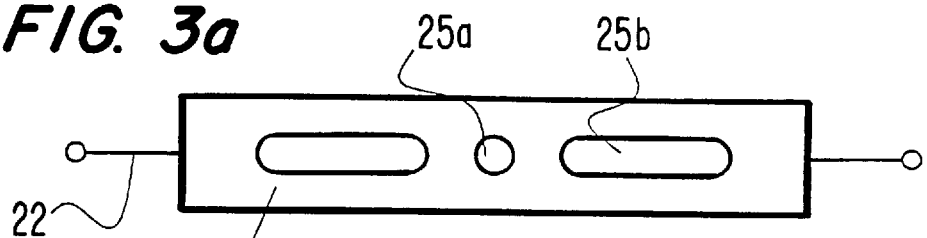
Figure 3B:
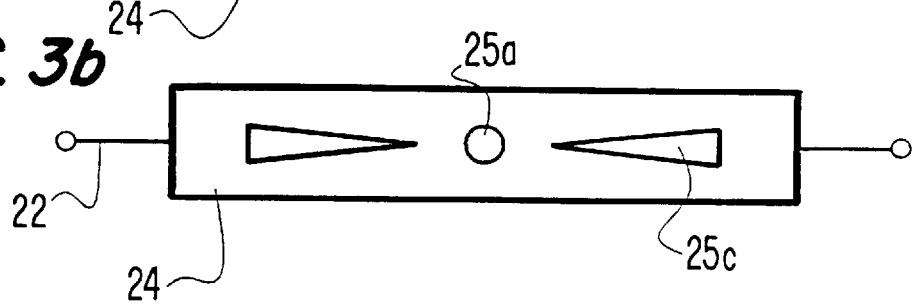
Figure 3C:
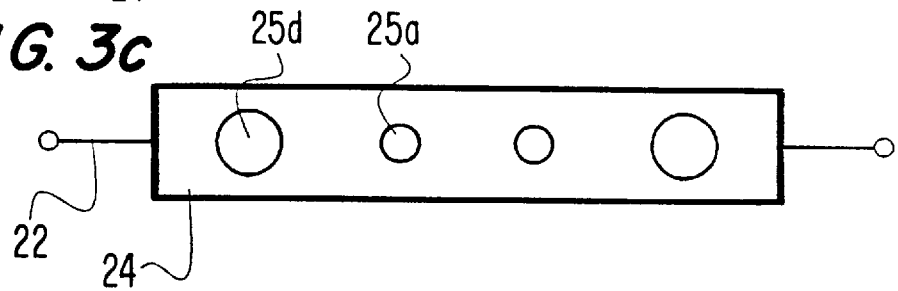
Figure 3D:
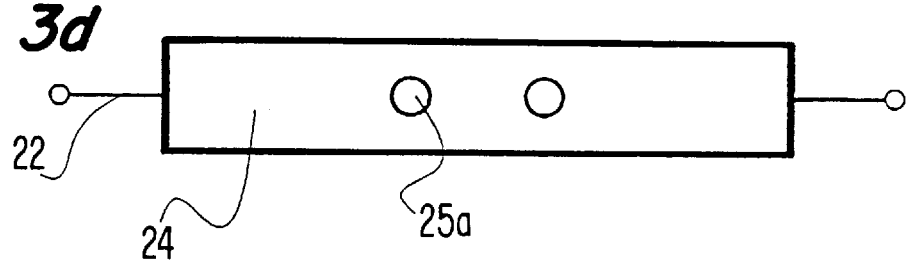
Figure 3E:
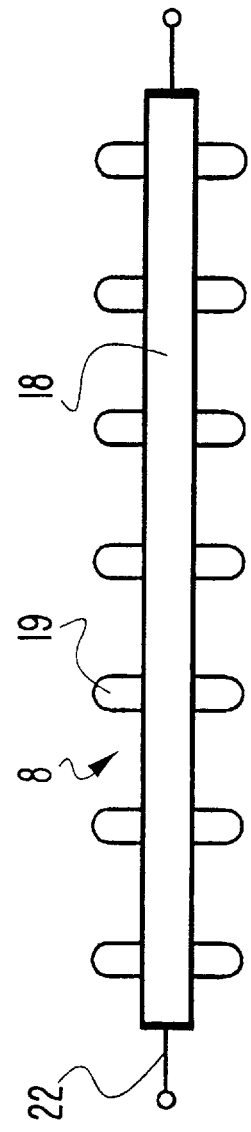
Figure 3F:
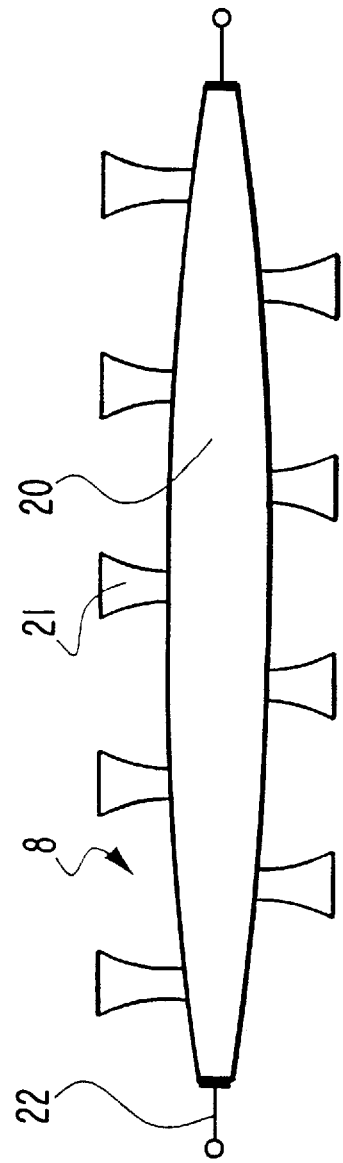

In the event that the electrical heating appliance 8 were to be designed as a compact cuboic heating element or, more particularly, as a thin-walled hollow body 18, 20 with linear or bulbous walls, the surface-area increasing nipples 19 or fingers 21 would facilitate increased heat transfer to the through-flowing air. At the same time a mechanically advantageous stabilisation of the heating element within the flow channel would be accomplished (FIGS. 3e and 3f).

Contacts 22 are provided for the connection of the heating appliance 8 to the control unit of the smoking device.

Figure 4:
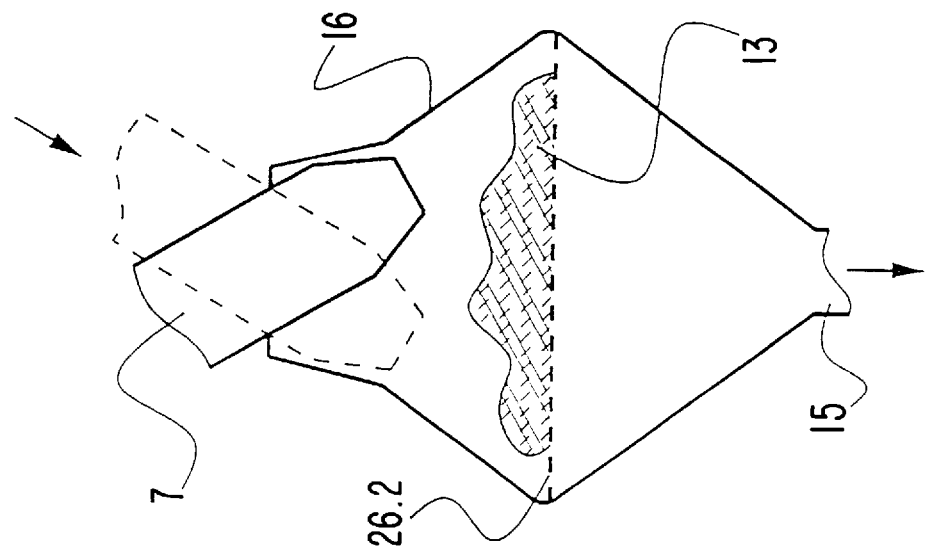
FIG. 4 shows another favourable embodiment of the invention in simplified depiction.
Figure 5:
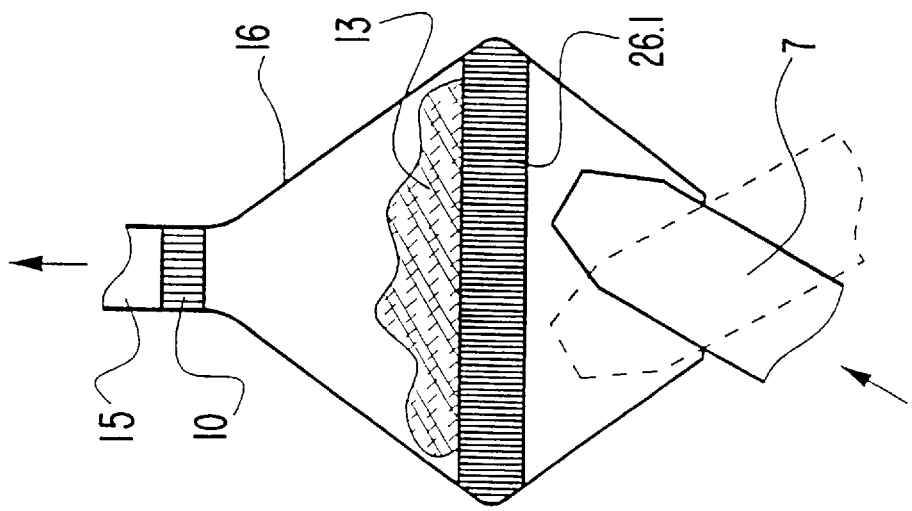
FIG. 5 is a schematic representation of a variation of the version in FIG. 4.

When the smoking product's position remains static, the relative movement between the hot air stream and the smoking product (necessary for the optimized exploitation of the latter) is effected by movement of the hot air stream. This is depicted, in cross-section, in FIGS. 4 and 5. The smoking product 13 is placed on a saucer-like, porous and permeable surface 26.1 or on a fine-meshed sieve 26.2. The hot air generator 7 is swivel-mounted in such a way that its air outlet nozzle Is able to be directed roughly onto the entire permeable surface 26.1 beneath the smoking product (FIG. 4) or directly onto the smoking product's entire surface as in FIG. 5.

Figure 6:
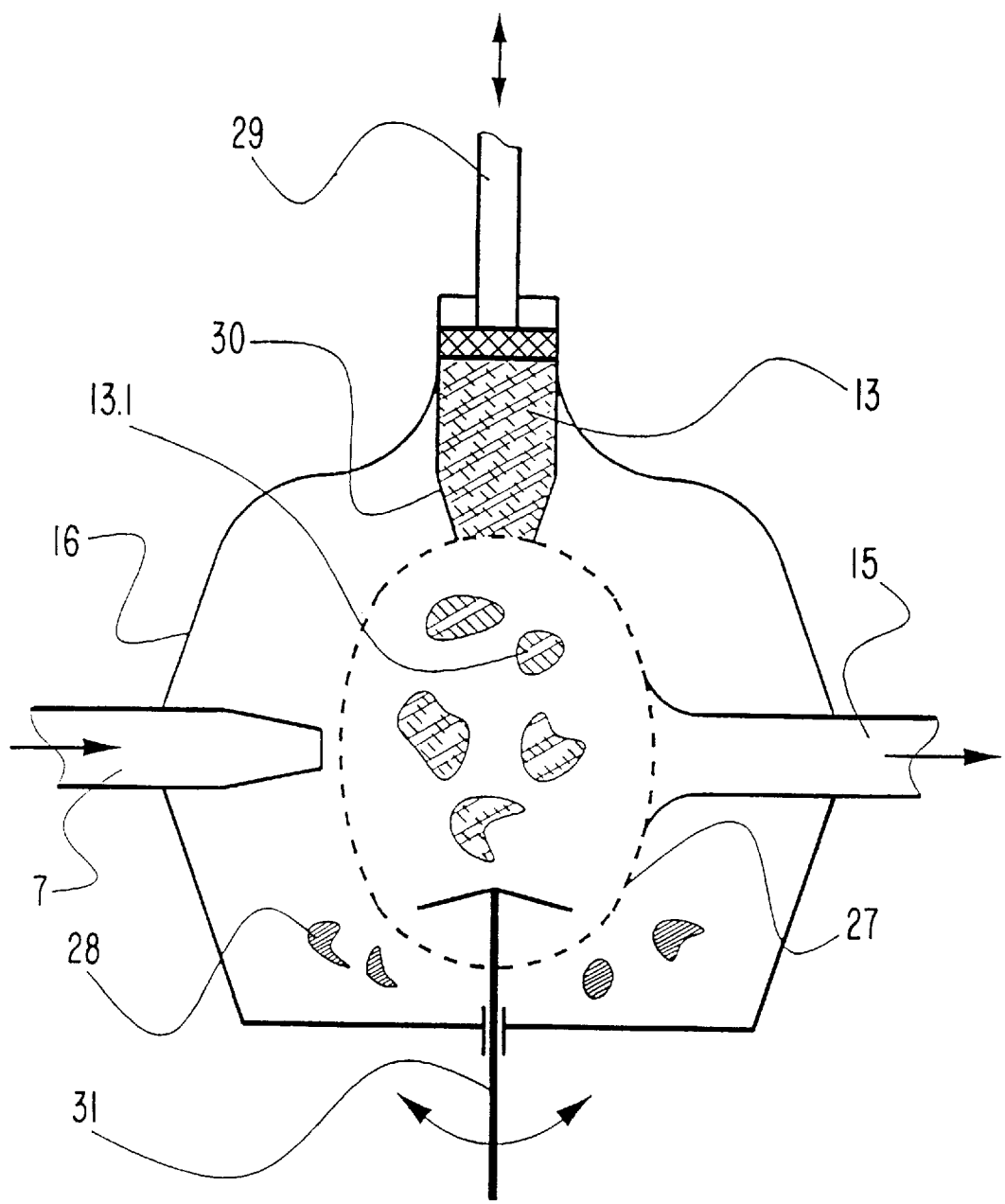
FIG. 6 is a further advantageous realization of the invention in cross-section.

FIG. 6 depicts a further subsequent conception of the invention in cross-section, whereby a quantity of smoking product 13 descends gravitationally (and becomes distributed into small amounts 13.1) via a pre-heatable reservoir 30 into a sieve-like storage compartment 27. Hot air from the hot air generator 7 is directed into the sieve-like storage compartment 27 substantially at right angles to the direction of the descending quantities of smoking product; in this way the relative movement between smoking product and hot air jet can be simply achieved and the smoking product thus optimally activated for the release of aerosols. An anchor-like swizzlestick 31 for stirring and kneading in the storage compartment 27 helps to rearrange the smoking product's particles and exposes them once again to the hot air stream before they at last leave the storage compartment 27 as consumed smoking product 28. Subsequently required smoking product is supplied by means of a plunger 29.

Figure 7:
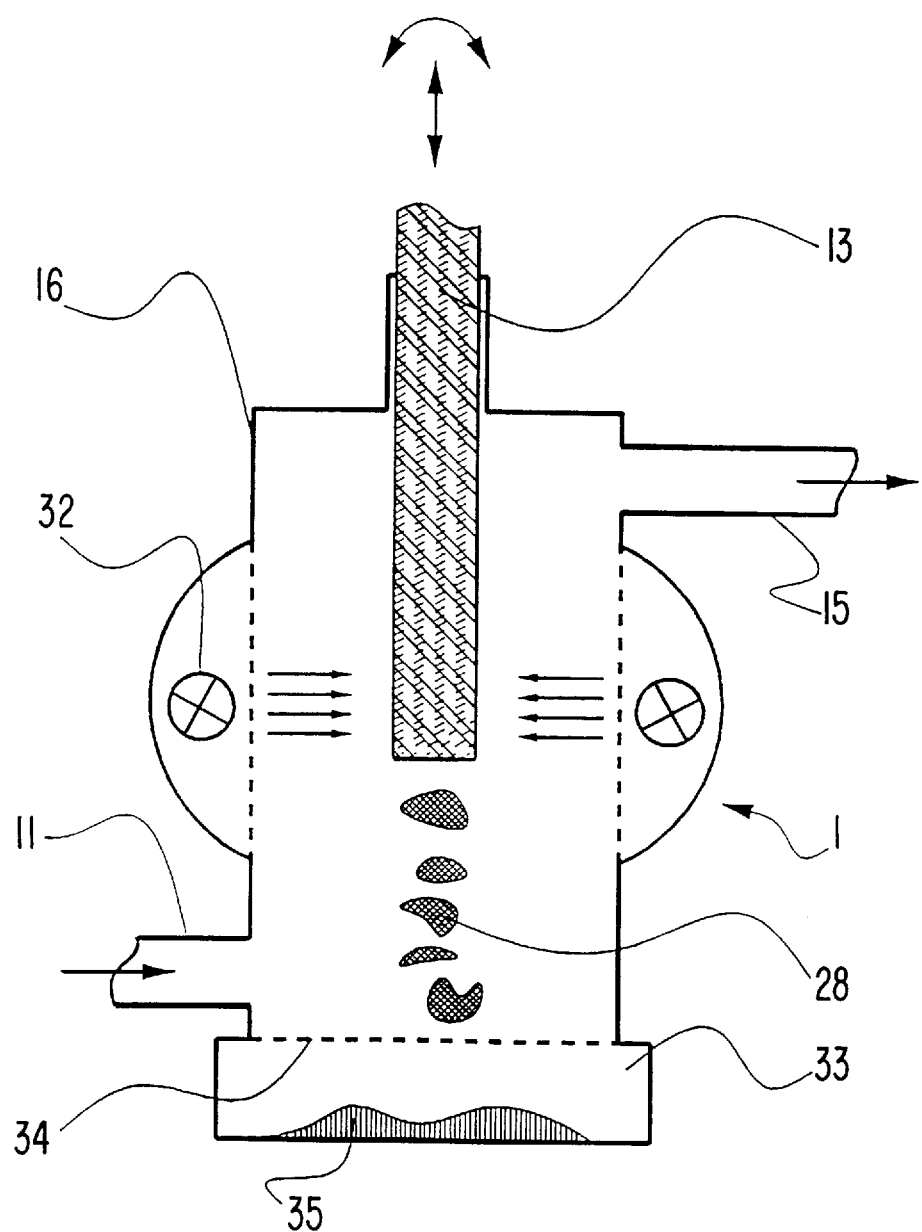
FIG. 7 is another advantageous embodiment of the invention in cross-section.

FIG. 7 depicts a variation of the smoking device fitted with radiation heating 32. The radiation transversely affects the smoking product 13 which descends into the smoking chamber 16 in smaller lots. The stick of smoking product "burns off" in a downward direction, starting from the top, to release the desired quantities of aerosols. Inhaled ambient air passing through the standpipe 11 flows in a direction opposite to the descent of the smoking product's subsequently consumed quantities 28, and reaches the smoker via the standpipe 15 enriched with aerosols. Regulation of radiation intensity is achieved in the same way as that of the heating current (as previously described), by measuring the quantity of consumed ambient air required for smoking. To reduce radiation power, it is advisable to preheat the air inhaled into the smoking chamber 16 by means of a previously described hot air generator (not depicted); consumed quantities 28 of the smoking product fall through a grille 34 into a reservoir 33 and are removed as ash-like waste 35.

In another variation of the device (not shown), the housing adjacent to the heating appliance would be transparent so that its glow would be visible when the heating is activated. The heating would, at best, be fixed to the end of the device farthest from the user in order to create the psychological impression of conventional smoking. This effect could also be obtained or enhanced by the appropriate use of a light-emitting diode (LED), most suitably red or orange, which would be activated with the heating appliance.

An additional advantageous subsequent development of the invention would enable the user to choose or shift the individual smoking profile to that of a cigarette or water pipe/hookah.

The principal subjective difference between these traditional smoking methods is that cigarette smokers inhale relatively small quantities of highly concentrated smoke through a mouthpiece or filter into the mouth and pharyngeal cavity. Further inhalation of fresh air then forces the smoke deeper into the lungs and bronchioles.

The water pipe or hookah, on the other hand, allows the user to inhale larger quantities of aerosols with conversely smaller quantities of fresh air thereafter.

Compared to a water pipe, cigarettes have a relatively high flow resistance. This causes the drawn-in cheeks and puckered lips typical to inhalation of cigarette smoke due to the (even at low flow rates) relatively high underpressure.

The invention's advantage is that it provides very low flow resistance. The experience of smoking is thus not unlike that of a large water pipe.

In order to achieve a more cigarette-like smoking profile, especially a soft silicon tube could be connected to the suction standpipe. This would allow the user, while smoking, to pinch the tube with the fingers and thus vary the amount and underpressure of smoke to be inhaled. In this way the decisive subjective-psychological advantages of traditional smoking methods would be simply and variably combined.

The invention's possibilities are, of course, not limited to the examples given here. A multitude of variations making use of and being within the scope of the invention could be imagineable, even those with fundamentally different construction methods.

I claim:

1. A device for inhaling an inhalable substance comprising:
   a reservoir defining a substantially closed chamber for containing a particulate including a smoking product;
   a hot carrier gas generator including a heating appliance for heating a carrier gas thereby generating hot carrier gas, the heating appliance defining an outlet communicating with the chamber of the reservoir for releasing a stream of hot carrier gas into the chamber;
   means for heating the particulate by convection to a temperature below a glow temperature thereof utilizing the stream of hot carrier gas such that the inhalable substance is released from the particulate;
   means for at least one of arranging and guiding particles of the particulate such that surfaces of the particles are directly affected by the stream of hot carrier gas; and
   means for warming volumes of particles of the particulates up to a temperature close to and lower than the glow temperature.

2. The device according to claim 1, wherein the reservoir includes a saucer-shaped surface disposed in the chamber for supporting the particulate such that the particulate is adapted to be distributed thereon in a substantially even and flat manner.

3. The device according to claim 1, further comprising a holding means including one of a mesh, a sieve and a grille and having a supporting surface made of a sintered metal, the holding means being adapted to hold the particulate in position in the reservoir and further being adapted to serve as a filter.

4. The device according to claim 3, wherein the holding means is disposed such that, when the hot carrier gas emerges from the outlet of the heating appliance, it passes through the supporting surface of the holding means before it strikes the particulate.

5. The device according to claim 1, wherein the reservoir is movable at least one of by rotation and by translation and further comprises at least one of:
   a shallow, cylinder open on one side thereof; and
   a flat cuboid defining a plurality of compartments.

6. The device according claim 1, wherein:
   the generator is disposed such that, when the hot carrier gas is emerging from the outlet of the heating appliance, the hot carrier gas substantially strikes an entire surface area of the reservoir covered with the particulate; and
   the heating appliance is a heating foil element.

7. The device according to claim 1, wherein the heating appliance is configured such that, when the hot carrier gas emerges from the outlet thereof, the hot carrier gas achieves a temperature above the glow temperature of the particulate for a period of time, measured utilizing thermal time constants, which period of time does not lead to a rise in temperature of the particulate to its glow temperature.

8. The device according to claim 1, further comprising control means programmable for maintaining a predetermined outflow temperature of the hot carrier gas from the outlet of the heating appliance, the control means comprising at least one of:
   means for adjusting a supply of auxiliary energy as a function of a quantity of gas flow through the heating appliance; and
   a pressure sensor for measuring a quantity of gas flow through the heating appliance.

9. The device according to claim 1, wherein the device defines a passage therein for allowing gravitationally descending sub-quantities of the particulate to pass therethrough and to cross the stream of hot carrier gas in a non-parallel flow direction.

10. The device according to claim 1, further comprising a housing which is transparent adjacent the heating appliance such that, visible through the housing is at least one of a heat glow of the heat appliance and an electrical light activated in response to an activation of the heating appliance.

11. The device according to claim 1, further comprising a suck-off channel having a contractible cross-section at a portion thereof, the portion being made of an elastomer deformable by finger pressure.

12. A device for inhaling an inhalable substance comprising:

a reservoir defining a substantially closed chamber for containing a particulate including a smoking product, the reservoir further defining:
   a suck-in opening for guiding a carrier gas about the particulate; and
   a suck-off opening for allowing the inhalable substance to be inhaled out of the reservoir;
a radiation heating appliance disposed for directly affecting the particulate in the reservoir; and
means for at least one of arranging and guiding particles of the particulate such that particles of the particulate are warmed up to a temperature close to and lower than the glow temperature and are streamed along by the carrier gas.

* * * * *